United States Patent [19]

Phillips et al.

[11] Patent Number: 5,190,723

[45] Date of Patent: Mar. 2, 1993

[54] PROCESS FOR INHIBITING CORROSION

[75] Inventors: Emyr Phillips, Wakefield; Robert C. Wasson, Warrington, both of England

[73] Assignee: Ciba-Geigy Corporation, Ardsley, N.Y.

[21] Appl. No.: 622,133

[22] Filed: Dec. 3, 1990

Related U.S. Application Data

[63] Continuation of Ser. No. 314,678, Feb. 23, 1989, abandoned.

[30] Foreign Application Priority Data

Feb. 25, 1988 [GB] United Kingdom ................. 8804457

[51] Int. Cl.$^5$ ............................................. C23F 11/10
[52] U.S. Cl. .......................................... 422/15; 422/7; 422/12; 422/13; 546/298; 546/301; 252/391; 252/392; 252/394; 252/395; 106/14.11; 106/14.31; 106/14.41; 106/14.42; 106/14.43
[58] Field of Search .................... 422/15, 7, 12, 13, 15; 546/298, 301; 252/47, 51.5 R, 391, 392, 395, 394; 106/14.11, 14.31, 14.41, 14.42, 14.43

[56] References Cited

U.S. PATENT DOCUMENTS

| | | |
|---|---|---|
| 2,388,058 | 10/1945 | Herlocker et al. |
| 2,944,086 | 7/1960 | Coffield et al. ................ 568/723 |
| 3,057,928 | 10/1962 | Koblitz et al. ................ 568/723 |
| 3,211,652 | 10/1965 | Hinkamp ........................ 568/723 |
| 3,452,038 | 6/1969 | Randell et al. .................... 422/7 |
| 3,491,155 | 1/1970 | O'Shea ........................... 568/47 |
| 3,531,414 | 9/1970 | Randell et al. ................ 252/392 |
| 3,637,863 | 1/1972 | Braus et al. .................... 568/52 |
| 3,709,883 | 1/1973 | Dexter et al. ................ 544/219 |
| 3,862,053 | 1/1975 | Susi ........................ 252/51.5 R |
| 4,020,113 | 4/1977 | Brindell et al. ................ 568/723 |
| 4,071,746 | 1/1978 | Quinlan ........................... 422/12 |
| 4,101,438 | 6/1978 | Fenier et al. ................. 252/395 |
| 4,221,839 | 9/1980 | de Graaf ........................ 106/16 |
| 4,329,381 | 5/1982 | Eschwey et al. ................ 427/386 |
| 4,358,616 | 11/1982 | Wedemeyer et al. ............ 568/49 |
| 4,828,616 | 5/1989 | Yamasoe ...................... 106/14.11 |
| 4,846,985 | 6/1989 | Rizvi et al. .................. 252/391 |

FOREIGN PATENT DOCUMENTS

| | | |
|---|---|---|
| 512872 | 5/1955 | Canada ........................... 106/16 |
| 0129506 | 12/1984 | European Pat. Off. |
| 0186255 | 7/1986 | European Pat. Off. |
| 459045 | 12/1936 | United Kingdom. |
| 806961 | 1/1959 | United Kingdom. |
| 1136539 | 12/1968 | United Kingdom. |

OTHER PUBLICATIONS

M. Tashiro et al., Chem. Abst. 86:155297(6) (1977).
B. Miller, Chem. Abst. 86:154876(c) (1977).
P. Bowman et al., Chem. Abst. 101:6720k (1984).
A. McKay et al., Chem. Abst. 60:1626(b) (1963).
C.A. 88:23774m.
J. Herdan et al., Rev. Roum. de Chem., 28(2), 129–137 (1983).
C.A. 97:197915j.

*Primary Examiner*—Robert J. Warden
*Assistant Examiner*—Laura E. Collins
*Attorney, Agent, or Firm*—Luther A. R. Hall

[57] ABSTRACT

A process for inhibiting corrosion involves new compositions which comprise an organic material and, a corrosion inhibitor which is a compound having the formula:

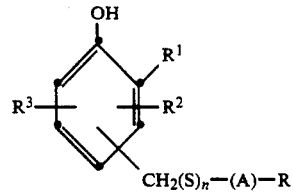

wherein
R$^1$ and R$^2$ may be the same or different and each is hydrogen, C$_1$-C$_{15}$alkyl, C$_3$-C$_{15}$alkenyl, C$_7$-C$_{10}$phenylalkyl, C$_6$-C$_{18}$aryl having 6 or 10 aromatic ring carbon atoms; or C$_5$-C$_{12}$cycloalkyl;
R$^3$ is hydrogen or C$_1$-C$_4$alkyl; n is 0 or 1;
A is a residue of a heterocyclic ring having 5–7 ring members and 1–4 nitrogen atoms, or A is a residue of a heterocyclic ring having 5–7 ring members and 1–4 nitrogen atoms and is fused to a further heterocyclic ring or to a carbocyclic ring, or A is a carbocyclic ring, in particular a phenyl or naphthyl ring, and wherein R is one or more of hydrogen, C$_1$-C$_{15}$alkyl, C$_1$-C$_4$halogenoalkyl, C$_1$-C$_{12}$alkoxy, C$_1$-C$_{12}$alkylthio, phenylthio, benzylthio, C$_1$-C$_{12}$alkylsulphonyl, phenyl, C$_7$-C$_{15}$alkylphenyl, C$_7$-C$_{10}$phenylalkyl, C$_5$-C$_8$cycloalkyl, halogen, NO$_2$, CN, COOH, COO(C$_1$-C$_{12}$alkyl), OH, NH$_2$, CONH$_2$, NHR$^4$, N(R$^4$)$_2$, (CONH(R$^4$) or —CON(R$^4$)$_2$ wherein R$^4$ is C$_1$-C$_{12}$alkyl, C$_3$-C$_{12}$alkyl which is interrupted by one or more O-atoms, C$_5$-C$_8$cycloalkyl, benzyl, phenyl or phenyl which is substituted by halogen, C$_1$-C$_4$alkyl, C$_1$-C$_4$alkoxy or NO$_2$, or N(R$^4$)$_2$ is a pyrrolidino, piperidino or morpholine group; provided that i) A is not benzothiazole residue; and ii) when A is a carbocyclic ring and n is 1, A is not 3,5-di-t-butyl-4-hydroxyphenyl and, when n is 1 and A is phenyl substituted by alkyl, R$_1$ and R$_2$ are not both t-butyl.

13 Claims, No Drawings

PROCESS FOR INHIBITING CORROSION

This is a continuation of application Ser. No. 314,678, filed on Feb. 23, 1989, now abandoned.

The present invention relates to new compositions, in particular to compositions comprising an organic material e.g. a coating material or lubricant a corrosion-inhibiting aromatic or heterocyclic compound containing a phenolic substituent.

In European Patent Specification No. 3817A, 2-mercaptobenzothiazole and its salts are disclosed as corrosion inhibitors. It is also known that various derivatives of 2-mercaptobenzothiazole exhibit corrosion-inhibiting properties. For example, European Patent Specification 129506A discloses benzothiazol-2-yl thiocarboxylic acids containing hydrophilic groups and their use as corrosion inhibitors.

We have now found, surprisingly, that certain aromatic or heterocyclic compounds containing a phenolic substituent carrying hydrophobic groups have, in addition to excellent corrosion-inhibiting properties, activity as antioxidants in organic materials especially coating materials or lubricants.

Accordingly, the present invention provides a composition comprising an organic material and, as corrosion inhibitor and/or antioxidant, at least one compound having the formula I:

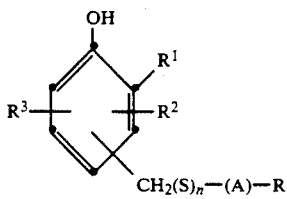

wherein
R$^1$ and R$^2$ may be the same or different and each is hydrogen, C$_1$–C$_{15}$alkyl, C$_3$–C$_{15}$alkenyl, C$_7$–C$_{10}$-phenylalkyl, C$_6$–C$_{18}$aryl having 6 or 10 aromatic ring carbon atoms; or C$_5$–C$_{12}$cycloalkyl;
R$^3$ is hydrogen, C$_1$–C$_{15}$alkyl or C$_2$–C$_{15}$alkenyl; n is 0 or 1; A is a residue of a heterocyclic ring having 5–7 ring members and 1–4 nitrogen atoms, or A is a residue of a heterocyclic ring having 5–7 ring members and 1–4 nitrogen atoms and is fused to a further heterocyclic ring or to a carbocyclic ring, or A is a carbocyclic ring, selected from the group, consisting of a phenyl or naphthyl ring, and wherein R is one or more of hydrogen, C$_1$–C$_{15}$alkyl, C$_1$–C$_4$halogenoalkyl, C$_1$–C$_{12}$alkoxy, C$_1$–C$_{12}$alkylthio, phenylthio, benzylthio, C$_1$–C$_{12}$alkylsulphonyl, phenyl, C$_7$–C$_{15}$alkylphenyl, C$_7$–C$_{10}$phenylalkyl, C$_5$–C$_8$cycloalkyl, halogen, NO$_2$, CN, COOH, COO(C$_1$–C$_{12}$alkyl), OH, NH$_2$, CONH$_2$, NHR$^4$, N(R$^4$)$_2$, CONH(R$^4$) or —CON(R$^4$)$_2$ wherein R$^4$ is C$_1$–C$_{12}$alkyl, C$_3$–C$_{12}$alkyl which is interrupted by one or more O-atoms, C$_5$–C$_8$cycloalkyl, benzyl, phenyl or phenyl which is substituted by halogen, C$_1$–C$_4$alkyl, C$_1$–C$_4$alkoxy or NO$_2$, or N(R$^4$)$_2$ is a pyrrolidino, piperidino or morpholine group; provided that i) A is not benzothiazole residue; and ii) when A is a carbocyclic ring and n is 1, A is not 3,5-di-t-butyl-4-hydroxyphenyl and, when n is 1 and A is phenyl substituted by alkyl, R$_1$ and R$_2$ are not both t-butyl.

When A is the residue of an N-containing 5–7 membered heterocycle or a heterocycle fused to a heterocyclic or carbocyclic ring other than a benzothiazole residue, it may contain one or more heteroatoms especially oxygen and sulphur atoms and may contain a substituent having the formula —C═X in which X is oxygen or sulphur, preferably sulphur.

When R, R$^1$, R$^2$, R$^3$ and R$^4$ are C$_1$–C$_{15}$alkyl such alkyl groups may be branched or unbranched. Specific examples of such alkyl groups include methyl, ethyl, n-propyl, isopropyl, n-butyl, sec-butyl, isobutyl, tert.butyl, pentyl, hexyl, n-octyl, 2-ethylhexyl, 1,1,3,3-tetramethylbutyl, 1,1,3,3,5,5-hexamethylhexyl, n-decyl, isodecyl, n-dodecyl and pentadecyl groups. R$^3$ may be preferably C$_1$–C$_4$alkyl groups and may be methyl, ethyl, n-propyl, isopropyl, n-butyl, sec.-butyl, isobutyl or tert.-butyl groups. Especially preferred for R$^3$ are hydrogen, methyl or pentadecyl groups. R$^3$ may be C$_2$–C$_{15}$alkenyl and preferably a pentadecenyl group. C$_7$–C$_{10}$phenylalkyl groups R$^1$, R$^2$ and R may be benzyl, 1-phenylethyl, 2-phenylethyl, α,α-dimethylbenzyl or 2-phenylpropyl groups.

Halogenoalkyl groups R may be e.g. chloromethyl, trichloromethyl, bromomethyl, 2-chloroethyl, 2,2,2-trichloromethyl, trifluoromethyl or 2,3-dichloropropyl.

As alkoxy, alkylthio or alkylsulphonyl, R may be methoxy, ethoxy, isopropoxy, butoxy, hexyloxy, octyloxy, dodecyloxy, methylthio, ethylthio, ethylthio, nonylthio, methylsulphonyl, ethylsulphonyl, hexylsulphonyl or dodecylsulphonyl.

Alkylphenyl groups R include tolyl, xylyl, 4-ethylphenyl, 4-tert.butylphenyl, 4-octylphenyl or 4-nonylphenyl. C$_5$–C$_8$cycloalkyl groups R or R$^4$ include cyclopentyl, cycloheptyl, methylcyclohexyl or cyclooctyl.

When R$^4$ is phenyl which is substituted by halogen, C$_1$–C$_4$alkyl, C$_1$–C$_4$-alkoxy or NO$_2$, R$^4$ may be 4-chlorophenyl, 3-bromophenyl, 2-fluorophenyl, p-tolyl, 3,5-dimethylphenyl, 4-isopropylphenyl, 4-methoxyphenyl, 3-ethoxyphenyl, 4-nitrophenyl or 4-nitro-2-methylphenyl.

When R$^4$ is C$_3$–C$_{12}$alkyl interrupted by one or more oxygen atoms, it may be 2-methoxyethyl, 2-butoxyethyl, 3,6-dioxaheptyl or 3,6-dioxadecyl.

N-containing heterocyclic residues A are mono- or bi-cyclic; when A is a bicyclic residue it consists of a heterocyclic ring fused to a further heterocyclic ring or to a carbocyclic ring.

Examples of optionally substituted monocyclic heterocyclic residues A include 1,2,4-triazole, imidazole, pyrazole, tetrazole, thiazolin-2-thione, imidazolin-2-thione, N-methyl-imidazolon-2-thione and 5-(3-phenyl-1,3,4-thia-diazol-2(3H)-thione), 2-pyridine, 4-pyridine, 3-pyridazine, 2-pyrimidine, 2-thiazole, 2-thiazoline, 3-(1,2,4-triazole) and 5-(2-mercapto-1,3,4-thiadiazole).

Examples of bicyclic, all-heterocyclic residues A are naphthyridine, purine and pteridine residues, while bicyclic heterocyclic-aromatic residues A include benzimidazole, benzotriazole, benzoxazolin-2-thione and 2-benzoxazole.

When A is a carbocyclic residue it is preferably an aromatic residue e.g. 1-naphthol, 2-naphthol, 2-aminophenol or phenol.

Preferred compositions according to the present invention include those containing a compound of formula I containing a residue A in which one, two or three R's and preferably one R, have their previous significance and the other R's are hydrogen.

Preferred compositions according to the present invention include those containing a compound of formula I containing a residue A in which one R is hydrogen, $C_1$-$C_4$alkyl, $C_1$-$C_4$alkoxy, trifluoromethyl, halogen or nitro and the other R's are hydrogen; $R^1$ is $C_1$-$C_8$alkyl, $C_7$-$C_{10}$phenylalkyl, phenyl or cyclohexyl; $R^2$ is hydrogen, $C_1$-$C_8$alkyl, $C_7$-$C_{10}$phenylalkyl, phenyl or cyclohexyl; and $R^3$ is hydrogen.

With respect to the compounds of formula I, the phenolic group is preferably positioned in the para- or ortho-position relative to the —$CH_2$—$(S)_n$—(A)—R group.

When the phenolic group is in the para-position to the —$CH_2$—(A)—R group, preferred compounds are those having the formula IA:

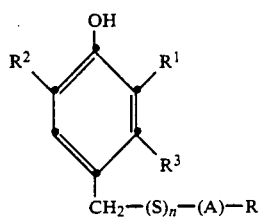

IA wherein R, $R^1$, $R^2$, $R^3$, n and A have their previous significance.

Preferred compounds of formula IA are those in which $R^1$ and $R^2$, independently, are hydrogen, $C_1$-$C_{15}$alkyl, $C_7$-$C_{10}$phenylalkyl, phenyl or cyclohexyl, and $R^3$ is hydrogen or methyl; more preferred compounds of formula IA are those wherein $R^1$ and $R^2$ are $C_1$-$C_5$alkyl and $R^3$ is hydrogen.

When the phenolic group is in the ortho-position to the —$CH_2$—(A)—R group, preferred compounds are those having the formula IB:

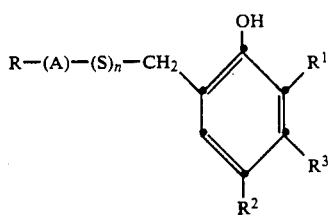

IB wherein R, $R^1$, $R^2$, $R^3$, n and A have their previous significance.

Preferred compounds of formula IB are those wherein $R^1$ is $C_1$-$C_8$alkyl, $C_1$-$C_4$alkoxy, $C_7$-$C_{10}$phenylalkyl, phenyl or cyclohexyl, and $R^2$ is hydrogen $C_1$-$C_8$alkyl, $C_7$-$C_{10}$phenylalkyl, phenyl, or cyclohexyl and $R^3$ and A have their previous significance.

More preferred compounds of formula IB are those wherein $R^1$ and $R^2$ are each $C_1$-$C_5$alkyl and $R^3$ and A have their previous significance.

Specific examples of compounds of formula IA are summarised in the following Tables 1 to 4:

i) where n is 0 and A is a residue of a heterocyclic ring or a heterocyclic ring fused to a carbocyclic ring:

TABLE 1

| A | R | $R^1$ | $R^2$ | $R^3$ |
|---|---|---|---|---|
| (triazole) | H | $t_{Bu}$ | $t_{Bu}$ | H |
|  | H | Ph | Ph | H |
|  | H | Me | Me | Me |
| (benzimidazole) | H | $t_{Bu}$ | $t_{Bu}$ | H |
|  | H | Me | Me | H |
|  | H | cyclohexyl | cyclohexyl | H |
| (imidazole) | H | $t_{Bu}$ | $t_{Bu}$ | H |
|  | H | Me | Me | H |
|  | H | Ph | Ph | H | ii) where n is 0, A is a residue of a heterocyclic ring or heterocyclic ring fused to a carbocyclic ring and containing a thione group:

TABLE 2

| A | R | $R^1$ | $R^2$ | $R^3$ |
|---|---|---|---|---|
| (benzoxazole-thione) | H | $t_{Bu}$ | $t_{Bu}$ | H |
|  | H | Ph | Ph | H |
|  | H | $t_{Bu}$ | Me | H |
|  | H | Me | Me | Me |
| (dithiolane) | H | $t_{Bu}$ | $t_{Bu}$ | H |
|  | H | $t_{Bu}$ | Me | H |
|  | H | Me | Me | Me |
| (N-Me thiazoline) | H | $t_{Bu}$ | $t_{Bu}$ | H |
|  | H | Me | Me | H |
|  | H | $t_{Bu}$ | $t_{Bu}$ | H |
| (pyridinethione) | H | $t_{Bu}$ | $t_{Bu}$ | H | iii) where n is 1, A is a residue of a monocyclic heterocylic ring:

TABLE 3

| A | R | R¹ | R² | R³ |
|---|---|---|---|---|
| (pyridine ring, R substituted) | H | tBu | tBu | H |
| | H | tBu | Me | H |
| | H | tBu | Pr | H |
| | 3-CO₂H | tBu | tBu | H |
| | H | Me | Me | Me |
| (pyridine ring, R substituted) | H | Ph | Ph | H |
| | H | tBu | tBu | H |
| | H | Me | Me | H |
| | H | Me | Me | Me |
| | H | tBu | Me | H |
| (thiadiazoline ring with R on N) | H | tBu | tBu | H |
| | Ph | tBu | tBu | H |
| | Ph | Me | Me | Me |
| | Ph | Me | Me | H |
| (imidazoline ring, R substituted) | H | tBu | tBu | H |
| | nC₄H₉ | tBu | tBu | H | iv) where n is 1 and A is a residue of a carbocyclic ring:

TABLE 4

| A | R | R¹ | R² | R³ |
|---|---|---|---|---|
| (benzene ring, R substituted) | H | tBu | tBu | H |
| | H | CH₃ | CH₃ | CH₃ |
| | 2-CH₃ | tBu | tBu | H |
| | H | iPr | iPr | H |
| | 2-NH₂ | tBu | tBu | H |
| | 2-CO₂H | tBu | tBu | H |
| (naphthalene ring, R substituted) | H | tBu | tBu | H |
| | H | CH₃ | CH₃ | CH₃ |
| | H | tBu | CH₃ | H |

Specific examples of compounds of formula IB are summarised in Tables 5 to 8:

i) where n is 0 and A is a residue of a heterocyclic ring or a heterocyclic ring fused to a carbocyclic ring:

TABLE 5

| A | R | R¹ | R² | R³ |
|---|---|---|---|---|
| (benzimidazole, R substituted) | H | tBu | tBu | H |
| | S-Me | tBu | tBu | H |
| | H | CH₃ | CH₃ | H |

TABLE 5-continued

| A | R | R¹ | R² | R³ |
|---|---|---|---|---|
| (pyrazole ring, R on N) | H | CH₃ | CH₃ | H |
| | H | tBu | tBu | H | ii) where n is 0 and A is a residue of a heterocyclic ring or heterocyclic ring and containing a thione group:

TABLE 6

| A | R | R¹ | R² | R³ |
|---|---|---|---|---|
| (benzoxazole-2-thione, R substituted) | H | tBu | tBu | H |
| | H | Me | Me | H |
| | H | Ph | Ph | H |
| (thiazolidine-2-thione, R on N) | H | tBu | Me | H |
| | H | tBu | tBu | H | iii) where n is 1, A is a residue of a heterocyclic ring:

TABLE 7

| A | R | R¹ | R² | R³ |
|---|---|---|---|---|
| (pyridine ring, R substituted) | H | tBu | tBu | H |
| | H | Me | Me | H |
| | 3-CO₂H | tBu | tBu | H |
| | 3-CO₂H | tBu | Me | H |
| (pyridine ring, R substituted) | H | tBu | tBu | H |
| | H | tBu | Me | H |
| | H | iPr | iPr | H | iv) where n is 1 and A is a residue of a carbocyclic ring:

TABLE 8

| A | R | R¹ | R² | R³ |
|---|---|---|---|---|
| (benzene ring, R substituted) | H | tBu | tBu | H |
| | H | Me | tBu | H |
| | H | Me | Me | H |
| | 2-NH₂ | tBu | tBu | H |
| | 2-CO₂H | tBu | tBu | H |

TABLE 8-continued

| | A | R | R¹ | R² | R³ |
|---|---|---|---|---|---|
| | 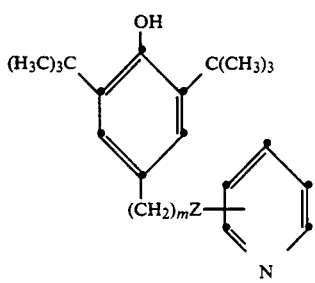 | H | tBu | tBu | H |

Those compounds of formula I and having the sub-generic formula:

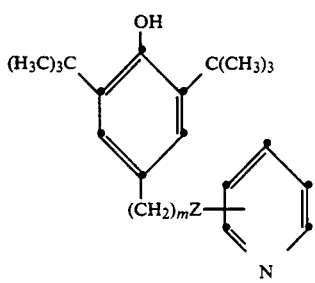

wherein Z is inter alia S and m is 0, 1 or 2 are known, and have been disclosed as antichloesteremics, hypolipemics and cerebal vasodilators in German Offenlegungsschrift 2,726,125.

Also known are those compounds of formula I have the sub-generic formulae:

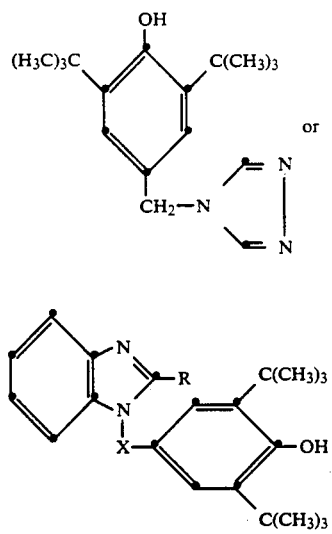

wherein X is CH₂ or SO₂; and R is hydrogen, methyl or —CH₂OH.

These compounds are disclosed as antioxidants in Rev. Roum. Chim. 1983, 28, 129–37.

Still further compounds of formula I having the sub-generic structure:

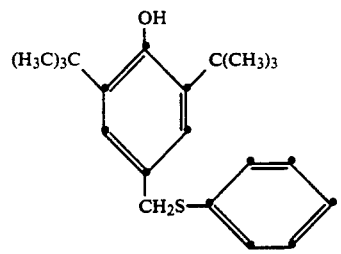

have been described as stabilisers and antioxidants for olefin polymers in U.S. Pat. No. 3,637,863.

All the other compounds of the formula I are novel compounds and, as such, form a further aspect of the present invention.

Accordingly the present invention also provides compounds having the formula I′

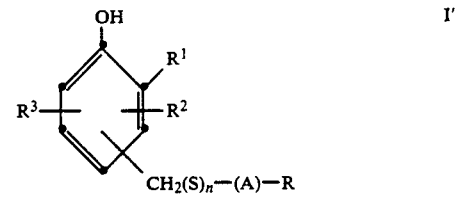

wherein R, R¹, R², R³, n and A have their previous significance, provided that:
i) A is not benzothiazole residue;
ii) when A is a carbocyclic ring and n is 1, A is not 3,5-di-t-butyl-4-hydroxyphenyl and, when n is 1 and A is phenyl substituted by alkyl, $R_1$ and $R_2$ are not both t-butyl;
iii) when n is 0 and A is a heterocyclic residue having 5–7 ring members and 1–4 nitrogen atoms, or A is a residue of a heterocyclic ring having 5–7 ring members and 1–4 nitrogen atoms and is fused to a further heterocyclic ring or to a carbocyclic ring, $R^2$ is H, $R^1$ and $R^3$ are each tert.-butyl and $R^3$ is in ortho-position to the —OH group, then A is not a 1,2,4-triazole ring or a benzimidazole ring substituted in the 2-position by methyl or hydroxymethyl;
iv) when n is 1 and A is a heterocyclic residue having 5–7 ring members and 1–4 nitrogen atoms, $R^2$ is H, $R^1$ and $R^3$ are each tert.-butyl and $R^3$ is in ortho-position to the —OH group, then A is not pyridinothio group; and
v) when n is 0 and A is a carbocyclic ring, $R^2$ is H, $R^1$ and $R^3$ are each tert.-butyl and $R^3$ is in ortho-position to the —OH group, then A is not a phenylthio residue.

The compounds of formula (I or I′) may be prepared by reacting in the presence of an acid catalyst a phenol compound having the formula II:

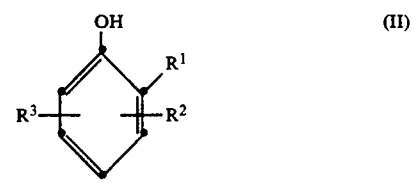

having at least one free position ortho- or para to the —OH group, wherein $R^1$, $R^2$ and $R^3$ have their previous significance, with formaldehyde and a precursor compound for the group A, wherein A has its previous significance.

The precursor compound for the group of formula A may be, for example, compound R—(A)—SH wherein R and A have their previous significance or a compound R—(A)—H and wherein R and A have their previous significance.

It will be appreciated that when the precursor compound has the formula R—(A)—SH then the residue R—(A)— in the compound of formula I so obtained may either be in the sulphide or thione form, the former being convertible into the latter by heating.

Heating can be carried out with or without a solvent.

Examples of suitable solvents are aromatic hydrocarbons, such as toluene or xylene; halogenated hydrocarbons, such as tetra-chloroethylene or chlorobenzene; alkanols, such as isopropanol or n-butanol; or esters, ketones, dimethylformamide or dimethyl sulfoxide. Polar solvents, for example dimethylformamide, accelerate the reaction. The rearrangement can also be accelerated by adding basic catalysts. Examples of the latter are, in particular, aliphatic, cycloaliphatic or heterocyclic amines. If the phenolic OH group is in the para-position relative to the radical —CH$_2$—, the rearrangement proceeds more rapidly than if the group is in the ortho-position. The temperature required for the rearrangement therefore depends on the position of the OH group and on the solvent and catalyst used. It is preferably carried out at 70°-250° C., in particular at 100°-200° C.

The compounds of formula (I or I') may also be prepared by reacting a phenol compound having the formula III:

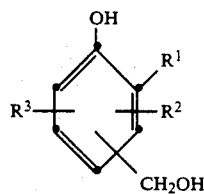

wherein $R^1$, $R^2$ and $R^3$ have their previous significance, with a precursor compound for the group R—(A)—, e.g. a compound having the formula R—(A)—SH or R—(A)—H.

A further process for the production of compounds of formula (I or I') comprises reacting a phenol compound of formula IV:

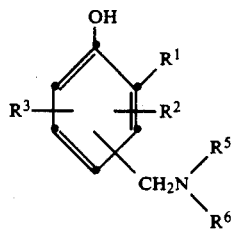

wherein $R^1$, $R^2$ and $R^3$ have their previous significance and $R^5$ and $R^6$, independently, are $C_1$-$C_{12}$alkyl, $C_5$-$C_8$-cycloalkyl, benzyl or phenyl, with a compound R—(A)—SH.

The reaction is preferably effected at elevated temperature e.g. 50°-200° C., especially 70°-150° C. and in the presence of a polar organic solvent e.g. a $C_1$-$C_4$alcohol, dimethylformamide or dimethylsulphoxide.

Another method for producing compounds of formula (I or I') comprises reacting in the presence of a basic catalyst, a phenol compound having the formula II:

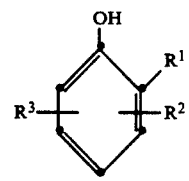

wherein $R^1$, $R^2$ and $R^3$ have their previous significance, with formaldehyde, and with a precursor compound for the group R—(A), e.g. a compound R—(A)—SH or R—(A)—H.

In this process also, isomeric compounds may be produced and conversion of sulphide compounds into thione compounds by heating, may be effected as indicated hereinbefore.

The reaction may be performed with or without solvent and preferably within the temperature range of 70°-150° C.

Any strong base may be used as catalyst, preferred examples include primary-, secondary- or tertiary amines such as isopropylamine, butylamine, cyclohexylamine, dibutylamine, dihexylamine, diisopropylamine, triethylamine, tributylamine, piperidine, morpholine, pyrrolidone or quinoline.

The formaldehyde used for the reaction may be, for example, an aqueous solution (formalin) in the form of paraformaldehyde, or a compound which releases formaldehyde, under the reaction conditions, for example hexa-methylene tetramine.

The compounds for the formula I are effective as corrosion inhibitors and as antioxidants. As such, they can be added to any liquid or solid organic materials. They are preferably used in coating materials or lubricants.

Examples of coating materials are lacquers, paints or varnishes. They always contain a film-forming binder as well as other optional components.

Examples of coating materials are materials based on a epoxide, polyurethane, aminoplast, acrylic, alkyd or polyester resin and on mixtures of such resins. Further examples of suitable binders are vinyl resins, such as polyvinyl acetate, polyvinylbutyral, polyvinyl chloride and copolymers thereof, cellulose esters, chlorinated rubbers, phenolic resins, styrene/butadiene copolymers and drying oils.

The coating materials can contain solvents or can be free from solvents or they can be aqueous systems (dispersions, emulsions or solutions). They can be pigmented or non-pigmented and they can be also be metallized. In addition to the corrosion inhibitors according to the invention, they can contain other additives customary in the technology of coating materials, for example fillers, flow control auxiliaries, dispersing auxiliaries, thixotropic agents, adhesion promoters, anti-oxidants, light stabilizers or curing catalysts. They can also contain other known anti-corrosion agents, for example anti-corrosion pigments, such as pigments containing phosphates or borates, or metal oxide pigments, or other organic or inorganic corrosion inhibitors, for example salts of nitroisophthalic acid, phosphorus esters, technical amines or substituted benzotriazoles.

It is also advantageous to add basic fillers or pigments which, in certain binder systems, produce a synergistic effect on the inhibition of corrosion. Examples of such basic fillers and pigments are calcium carbonate, magnesium carbonate, zinc oxide, zinc carbonate, zinc phosphate, magnesium oxide, aluminium oxide, aluminium phosphate or mixtures thereof. Examples of basic organic pigments are pigments based on aminoanthraquinone.

The corrosion inhibitor can also be applied to a carrier. Pulverulent fillers or pigments are particularly suitable for this purpose. This technique is described in greater detail in German Patent A 3,122,907.

The corrosion inhibitors can be added to the coating material during its preparation, for example during the dispersion of pigments by grinding, or the inhibitor is dissolved in a solvent beforehand and the solution is stirred into the coating agent. The inhibitors is used in an amount of 0.1 to 20% by weight, preferably 0.5 to 5% by weight, based on the solids content of the coating material.

The coating materials can be applied to the substrate by the customary process, for example by spraying, dipping, brushing or by electrodeposition, in particular cathodic dip-coating. Several layers are often applied. The corrosion inhibitors are added primarily to the base layer, since they act particularly on the metal/coating interface. It is also possible, however, additionally to add the inhibitors to the top layer or intermediate layer, where they are available as a depot. Depending on whether the binder is a physically drying resin or a heat-curable or radiation-curable resin, the coating is cured at room temperature or by heating (stoving) or by irradiation.

The coating material is preferably a primer for metallic substrates e.g. iron, steel, copper, zinc or aluminium. The coating material can be an aqueous system especially a cathodically-depositable paint (cataphores lacquer).

It is a particular advantage of the compounds of the formula I that they do not tend to become chalky. It is a further advantage that they have a favourable effect on the adhesion of coating to metal and, finally, that they exert an antioxidative action on the coating and thus reduce the chalking of pigments and fillers. All these properties contribute towards prolonging the useful life of the coating.

Examples of lubricants to which the corrosion inhibitors according to the invention can be added are lubricating oils and lubricating greases. The lubricating oils can be mineral oils of synthetic oils or mixtures of both. Examples of synthetic oils are those based on phosphoric acid esters, polyalkylene oxides, α-olefin polymers, triesters of trimethylolpropane or tetraesters of pentaerythritol or aliphatic polyesters.

The lubricants can contain further additives, for example antioxidants, pour-point depressants, viscosity index improvers, metal deactivators, dispersing agents, high-pressure additives or anti-wear additives. They can also contain other corrosion inhibitors, for example organic acids and esters, metal salts, amine salts or anhydrides thereof, heterocyclic compounds, phosphoric acid part esters and amine salts thereof or metal salts of sulfonic acids.

It is of considerable importance for the use of the compounds of the formula I in lubricants that these compounds also act an antioxidants, since multi-purpose additives are particularly valuable in this field.

The compounds of the formula I are used in lubricants in an amount of 0.01 to 5% by weight, in particular 0.2 to 2% by weight.

Both for coating materials and for lubricants it can be important to add a mixture of several compounds of the formula I. For example, if certain technical mixtures of phenols are used in the preparation of the compounds of the formula I, a mixture of products of the formula I is inevitably formed, and this can be used as such. However, in order to lower the melting point it can also be advantageous to mix two or more of such compounds.

Relative to known corrosion inhibitors, the compounds of formula I exhibit lower water absorption, chemical inertness and higher stability to heat.

The preparation and use of compounds of the formula I are described in greater detail in the following Examples. In these parts and percentages are by weight, unless stated otherwise. The temperatures is quoted in °C.

EXAMPLE 1

(3,5-Ditertbutyl-4-hydroxybenzyl)-4-mercaptopyridine

4-Mercaptopyridine (11.1 g, 0.1 mol), 2,6-di-tert-butylphenol (20,6 g, 0.1 mol), paraformaldehyde (3.0 g, 0.1M) and di-n-butylamine (1 ml) are heated at 80° C. for two and half hours, after which time, thin layer chromatography (t.l.c.) showed the reaction to be complete. The reaction mixture is cooled to 50° C., ethanol (100 ml) is added and the product is crystallised as a pale yellow solid (24.7 g, 78.4% of theory) of m.p. 169°–171° C. (Found C=73.30; H=8.49; N=4.31; S=9.71 $C_{20}H_{27}NOS$ requires C=72.95; H=8.21; N=4.26 and S=9.73%).

EXAMPLE 2

(3,5-Di-tert-butyl-4-hydroxybenzyl)-3-mercapto-1,2,4-triazole

3-Mercapto-1,2,4-triazole (20.2 g, 0.2 mol), 2,6-di-tertbutylphenol (41.2 g, 0.2 mol), paraformaldehyde (6.0 g, 0.2M) and di-n-butylamine (2 ml) are heated, under reflux, in ethanol (100 ml) for ten hours. The reaction mixture is cooled, and the product is crystalised as a white solid (43 g, 67% of theory) having a m.p. of 184°–185° C. (Found C=63.39; H=8.03; N=13.29; S=10.20 $C_{17}H_{25}N_3OS$ requires C=63.95; H=7.84; N=13.17 and S=10.03%).

EXAMPLE 3

(3,5-Di-tert-butyl-4-hydroxybenzyl)-2-mercaptonaphthalene

Thio-2-naphthol (16.0 g, 0.1 mol), 2,6-di-tertbutylphenol (20.6 g, 0.1 mol), paraformaldehyde (3.0 g, 0.1 mol) and di-n-butylamine (1 ml) in ethanol (100 ml) are heated, under reflux for thirteen hours, after which time thin layer chromatography shows the reaction to be complete. A small amount of solid impurity is filtered off and the solvent removed by rotary evaporation. A yellow oil is left which solidifies below 30° C. Petroleum (40°–60°) is added and a white solid (20.9 g, 55% of theory) of m.p. 30° C. is collected.

EXAMPLE 4

(3,5-Di-tert-butyl-4-hydroxybenzyl)-5-mercapto-3-phenyl-1,3,4-thiadiazole-2(3H) thione 5-Mercapto-3-phenyl-1,3,4-thiadiazole-2(3H) thione potassium salt (26.4 g, 0.1 mol), 2,6-di-tertbutylphenol (20.6 g, 0.1 mol), formalin (11 ml) and concentrated sulphuric acid (10 ml) in ethanol (100 ml) are heated, under reflux, for six hours. After this time, the ethanol is removed by rotary evaporation, and partitioned between ethyl acetate and water. The organic phase is dried over magnesium sulphate, filtered and the solvent removed in vacuo. A yellow oil is left (29.5 g, 66% of theory).

EXAMPLE 5

(3,5-Di-tert-butyl-4-hydroxybenzyl)-3-thiazoline-2-thione

2-Mercaptothiozoline (23.8 g, 0.2 mol), 2,6-di-tert-butylphenol (20.6 g, 0.2 mol), paraformaldehyde (6 g, 0.2 mol) and di-n-butylamine (1 ml) are heated, under nitrogen, at 180° C. for two hours. After this time, the reaction is cooled to 70° and ethanol (200 ml) is added. The product crystallises as a white solid (48 g, 71% of theory) of m.p. 138°–140° C. (Found C=63.95; H=8.14; N=4.13; S=18.61 $C_{18}H_{27}NOS_2$ requires C=64.09; H=8.01; N=4.15; S=18.99%).

EXAMPLE 6

(3-Tertbutyl-5-methyl-4-hydroxybenzyl)-benzoxazolin-2-thione

2-Mercaptobenzoxazole (10.96 g, 0.073 mol), 2-tert-butyl-6-methylphenol (11.9 g, 0.073 mol), paraformaldehyde (2.18 g, 0.073 mol) and di-n-butylamine (0.5 ml) are heated to 120° C. After two hours, the reaction mixture solidifies. The solid mass is crystallised from ethanol to yield a white solid (19.8 g, 84% of theory) of m.p. 155°–157° C. (Found N=4.17; $C_{19}H_{21}NO_2S$ requires N=4.28%).

EXAMPLE 7

1-(3,5-Di-tert-butyl-4-hydroxybenzyl)-1,2,4-triazole 1,2,4-Triazole (21.39 g, 0.31 mol) 2,6-di-tert-butylphenol (63.86 g, 0.3 mol), and paraformaldehyde (9.3 g, 0.31 mol) are heated to 100° C. for eight hours, after which time thin layer chromatography shows the reaction to be complete. On cooling, the reaction mass forms a wazy solid of m.p. <30° C. in quantitative yield.

EXAMPLES 8 TO 29

Using the procedure described in Example 1, the compounds summarised in the following Table 1 are prepared:

Examples indicating IA are those having the formula IA as described above, examples indicating IB are those having formula IB as described above.

TABLE I

| Example | A | R | $R_1$ | $R_2$ | $R_3$ | n | |
|---|---|---|---|---|---|---|---|
| 8 | | H | t-butyl | t-butyl | H | 1 | IA |
| 9 | | H | t-butyl | t-butyl | H | 1 | IA |
| 10 | | H | t-butyl | methyl | H | 1 | IB |
| 11 | | H | methyl | methyl | methyl | 1 | IA |
| 12 | | $CO_2H$ | t-butyl | t-butyl | H | 1 | IA |
| 13 | | $CO_2H$ | t-butyl | t-butyl | H | 1 | IA |

TABLE I-continued

| Example | A | R | R₁ | R₂ | R₃ | n | |
|---|---|---|---|---|---|---|---|
| 14 | (thiazolidine-2-thione ring) | H | H | H | $C_{15}H_{27}$ | 1 | IB |
| 15 | (benzoxazole) | H | t-butyl | methyl | H | 1 | IB |
| 16 | (benzoxazole) | H | methyl | methyl | methyl | 1 | IB |
| 17 | (benzoxazole) | H | t-butyl | t-butyl | H | 1 | IB |
| 18 | (N-methyl benzoxazole-2-thione) | H | H | H | $C_{15}H_{27}$ | 1 | IB |
| 19 | (N-methyl benzoxazol-2-one) | H | t-butyl | t-butyl | H | 1 | IA |
| 20 | (N-methyl benzoxazole-2-thione) | H | isopropyl | isopropyl | H | 1 | IA |
| 21 | (benzoxazole) | H | isopropyl | isopropyl | H | 1 | IB |
| 22 | (N-methyl benzoxazole-2-thione) | H | methyl | methyl | methyl | 1 | IB |

TABLE I-continued

| Example | A | R | R₁ | R₂ | R₃ | n | |
|---------|---|---|----|----|----|---|---|
| 23 | benzoxazole-2-thione | H | t-butyl | t-butyl | H | 1 | IA |
| 24 | 2-methoxy-benzothiazole | H | t-butyl | methyl | H | 1 | IB |
| 25 | benzoxazole-2-thione | H | methyl | t-butyl | H | 1 | IA |
| 26 | thiazole-2-thione | H | t-butyl | t-butyl | H | 1 | IA |
| 27 | triazole-thione | H | t-butyl | t-butyl | H | 1 | IA |
| 28 | N-methyl imidazole-thione | H | t-butyl | t-butyl | H | 1 | IA |
| 29 | thiazolidine-2-thione | H | t-butyl | t-butyl | H | 1 | IA |
| 30 | morpholine | H | H | H | $C_{15}H_{31}$ | 0 | IA |

Analytically data relating to the compounds of Examples 8 to 29 are set out in the following Table IA:

TABLE IA

| Example | Mpt °C. | Analysis |
|---------|---------|----------|
| 8 | 132–4 | ¹HNMR(CDCl₃) δ1.95(18H), δ4.25(2H), δ6.75(1H), δ7.10(2H), δ8.30(2H) Elemental analysis |

TABLE IA-continued

| Example | Mpt °C. | Analysis |
|---------|---------|----------|
|  |  | C, 69.52; H, 8.04; N, 8.51; S, 9.59% Theory |
| 9 | 98–9 | C, 69.09; H, 7.89; N, 8.48; s 9.70% ¹HNMR(CDCl₃) δ1.41(18H), δ4.35(2H), δ6.75(1H), δ6.85(1H), δ7.10(2H) |

TABLE IA-continued

| Example | Mpt °C. | Analysis |
|---|---|---|
| | | δ7.25(1H), δ8.25(1H) |
| | | Elemental analysis |
| | | C, 73.25; H, 8.29; N, 4.32% |
| | | Theory |
| | | C, 73.95; H, 8.21; N, 4.26% |
| 10 | 187-8 | ¹HNMR(DMSO$^{d6}$) δ1.38(9H), δ2.15(3H), δ4.35(2H), δ7.0(2H), δ7.35(2H), δ8.39(2H) |
| | | Elemental analysis |
| | | C, 70.09; H, 7.38; N, 4.88; S, 11.15% |
| | | Theory |
| | | C, 71.08; H, 7.32; N, 4.85; S, 11.41% |
| 12 | 208-9 | ¹HNMR(DMSO$^{d6}$) δ1.35(18H), δ4.21(2H), δ6.92(1H), δ7.15(2H), δ8.10(1H), δ8.45(1H) |
| 13 | 206-7 | ¹HNMR(CDCl₃) δ1.32(18H), δ3.95(2H), δ6.95(3H), δ7.19(2H), δ7.70(2H) |
| 14 | — | ¹HNMR(CDCl₃) δ1.0-2.8(27H), δ3.2(2H), δ3.90(2H), δ5.4(2H), δ6.7(1H), δ7.0(2H) |
| 15 | 84-5 | ¹HNMR(CDCl₃) δ1.39(9H), δ2.15(3H), δ4.35(2H), δ6.80(2H), δ7.0-7.5(4H) |
| 16 | 174-7 | ¹HNMR(CDCl₃/DMSO$^{d6}$) δ2.17(9H), δ5.2(2H), δ6.9-7.4(5H) |
| 17 | 115-9 | ¹HNMR(CDCl₃) δ1.3(9H), δ1.45(9H), δ4.4(2H), δ6.95-7.15(5H) |
| 18 | viscous oil | ¹HNMR(CDCl₃) δ1.15(21H), δ2.0-3.0(6H), δ5.25(2H), δ6.5-7.5(7H) |
| 19 | 136.5-137 | ¹HNMR(CDCl₃) δ1.19(18H), δ4.85(2H), δ6.9-7.1(6H) |
| 20 | 117-8 | ¹HNMR(CDCl₃) δ1.15-1.25(6H), δ2.05(2H), δ5.19(2H), δ6.95(6H) |
| 21 | 97-9 | ¹HNMR(CDCl₃) δ1.15(6H), δ2.75(2H), δ3.20(1H), δ4.38(2H), δ6.85-7.60(6H) |
| 22 | 209-212 | ¹HNMR(DMSO$^{d6}$) δ2.10(9H), δ5.15(2H), δ6.60-7.55(5H) |
| | | Elemental analysis |
| | | C, 67.18; H, 5.65; N, 4.92; S, 10.91% |
| | | Theory |
| | | C, 68.23; H, 5.69; N, 4.68; |
| 23 | 151-2 | ¹HNMR(CDCl₃) δ1.35(18H), δ5.20(2H), δ7.15(6H) |
| | | Elemental analysis |
| | | C, 71.54; H, 7.37; N, 3.75; S, 8.41% |
| | | Theory |
| | | C, 71.55; H, 7.32; N, 3.79; S, 8.67% |
| 24 | 169-70 | ¹HNMR(CDCl₃) δ1.35(9H), δ2.20(3H), δ4.90(2H), δ6.90-7.30(6H) |
| | | Elemental analysis |
| | | C, 69.24; H, 6.36; N, 4.26; S, 9.21% |
| | | Theory |
| | | C, 69.72; H, 6.42; N, 4.28; S, 9.78% |
| 25 | 155-7 | ¹HNMR(CDCl₃) δ1.19(9H), δ2.15(3H), δ5.20(2H), δ6.90-7.20(6H) |
| | | Elemental analysis |
| | | C, 68.50; H, 6.04; N, 4.17% |
| | | Theory |
| | | C, 69.72; H, 6.42; N, 4.28% |
| 26 | — | ¹HNMR(CDCl₃) δ1.40(18H), δ5.05(2H), δ6.75(2H), δ6.95(2H) |
| 27 | — | ¹HNMR(CDCl₃) δ1.40(18H), δ5.00(2H), δ6.98(3H) |
| 28 | 128-9 | ¹HNMR(CDCl₃) δ1.38(18H), δ3.50(3H), δ5.00(2H), δ6.45(2H), δ7.0(2H) |
| | | Elemental analysis |
| | | C, 68.41; H, 8.73; N, 8.46; S, 9.90% |
| | | Theory |
| | | C, 68.67; H, 8.43; N, 8.43; S, 9.64% |
| 29 | 138-140 | ¹HNMR(CDCl₃) δ1.40(18H), δ3.20(2H), δ4.00(2H), δ4.85(2H), δ7.15(2H) |
| | | Elemental analysis |
| | | C, 63.95; H, 8.14; N, 4.13; S, 18.61% |
| | | Theory |
| | | C, 64.09; H, 8.01; N, 4.15; S, 18.99% |
| 30 | ~30 | ¹HNMR(CDCl₃) δ0.82-1.21(27H), δ2.2-2.62(8H), δ3.45-3.65(6H), δ6.35-6.95(3H) |
| | | Elemental analysis |
| | | C, 77.35; H, 11.37; N, 3.45% |
| | | Theory |
| | | C, 77.42; H, 11.07; N, 3.47% |

EXAMPLES 30 TO 58

An alkyd resin paint is prepared in accordance with the following formulation:

40 parts of Alphthalate ® 380 (60% solution in xylene), alkyd resin made by Reichhold Albert Chemie AG, 10 parts of iron oxide red 224 made by Bayer AG, 13.6 parts of talc (micronized), 13 parts of micronized calcium (Millicarb ®, Pluss-Staufer AG), 0.3 part of skin prevention agent Luaktin ® 9 BASF), 0.6 part of 8% solution of cobalt naphthenate and 22.5 parts of 6:40 xylene/ethyleneglycol mixture.

The paint is ground with glass beads to a pigment and filler particle size of 10–15 μm. The corrosion inhibitors indicated in the tables below are added before grinding.

The paint is sprayed into sand-blasted steel sheets measuring 7×13 cm in a layer thickness amounting to approximately 50 μm after drying. After drying at room temperature for 7 days, the samples are subjected to after-curing at 60° for 60 minutes.

Two cruciform cuts of length 4 cm are cut, down to the metal, in the cured paint surface by means of a Bonder cross-cut apparatus. The edges are protected by applying an edge-protection agent (Icosit ® 255) to the latter.

The samples are now subjected to a salt spray test as specified in ASTM B 117 of a duration of 600 hours. After every 200 hours weathering, the state of the coating is assesed, specifically the degree of bubbling (as specified in DIN 53,209) at the cross-cut and on the painted surface and also the degree of rusting (as specified in DIN 53,210) on the whole surface.

At the end of the tests, the coating is removed by treatment with concentrated sodium hydroxide solution, and the corrosion of the metal at the cross-cut (as specified in DIN 53,167) and over the remainder of the surface is assessed. In each case the assessment is carried out in accordance with a 6-point scale. The sum of the assessment of the coating and the assessment of the metal surface gives the anti-corrosion value AC. The higher this is the more effective is the inhibitor tested.

TABLE II

Results of the Salt Spray Test

| Example | Corrosion Inhibitor | Amount added | Assessment of coating | Assessment of metal | AC |
|---|---|---|---|---|---|
| — | None | — | 2.2 | 0.6 | 2.8 |
| 30 | Product of | 2% | 5.0 | 5.2 | 10.2 |

TABLE II-continued
Results of the Salt Spray Test

| Example | Corrosion Inhibitor | Amount added | Assessment of coating | Assessment of metal | AC |
|---|---|---|---|---|---|
| | Example 1 | 4% | 5.4 | 5.0 | 10.4 |
| 31 | Product of Example 2 | 2%<br>4% | 2.2<br>2.4 | 4.0<br>4.2 | 6.2<br>6.6 |
| 32 | Product of Example 3 | 2% | 4.5 | 4.5 | 9.0 |
| 33 | Product of Example 4 | 2% | 4.1 | 4.3 | 8.4 |
| 34 | Product of Example 5 | 2%<br>4% | 4.9<br>3.9 | 3.7<br>4.0 | 8.6<br>7.9 |
| 35 | Product of Example 6 | 2%<br>4% | 4.8<br>3.7 | 4.7<br>3.7 | 9.5<br>7.4 |
| 36 | Product of Example 7 | 2%<br>4% | 2.5<br>2.2 | 3.9<br>3.9 | 6.4<br>6.1 |
| 37 | Product of Example 8 | 2% | 2.5 | 3.2 | 5.7 |
| 38 | Product of Example 9 | 2% | 2.7 | 2.9 | 5.6 |
| 39 | Product of Example 10 | 2% | 1.8 | 1.7 | 3.5 |
| 40 | Product of Example 11 | 2% | 2.4 | 2.0 | 4.4 |
| 41 | Product of Example 12 | 2% | 2.4 | 3.8 | 6.2 |
| 42 | Product of Example 13 | 2% | 1.8 | 1.3 | 3.1 |
| 43 | Product of Example 14 | 2% | 3.4 | 2.5 | 5.9 |
| 44 | Product of Example 15 | 2% | 2.6 | 2.5 | 5.1 |
| 45 | Product of Example 16 | 2% | 3.8 | 4.0 | 7.8 |
| 46 | Product of Example 17 | 2% | 3.7 | 2.9 | 6.6 |
| 47 | Product of Example 18 | 2% | 3.3 | 2.8 | 6.1 |
| 48 | Product of Example 19 | 2% | 2.2 | 3.9 | 6.1 |
| 49 | Product of Example 20 | 2% | 3.8 | 4.0 | 7.8 |
| 50 | Product of Example 21 | 2% | 3.5 | 2.6 | 6.1 |
| 51 | Product of Example 22 | 2% | 3.0 | 1.9 | 4.9 |
| 52 | Product of Example 23 | 2% | 2.8 | 2.7 | 5.5 |
| 53 | Product of Example 24 | 2% | 2.9 | 1.5 | 4.4 |
| 54 | Product of Example 25 | 2% | 4.8 | 4.7 | 9.5 |
| 55 | Product of Example 26 | 2% | 2.0 | 2.5 | 4.5 |
| 56 | Product of Example 27 | 2% | 2.4 | 4.1 | 6.5 |
| 57 | Product of Example 28 | 2% | 1.9 | 2.6 | 4.5 |
| 58 | Product of Example 29 | 2% | 4.9 | 3.7 | 8.6 |

What is claimed is:

1. A process for inhibiting corrosion of a metallic surface in contact with an organic material which comprises providing a corrosion-inhibiting effective amount of a compound of formula I

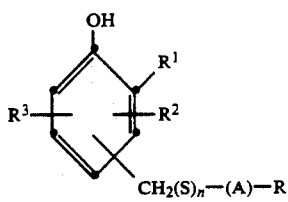

wherein

R$^1$ and R$^2$ are the same or different and each is hydrogen, C$_1$-C$_{15}$alkyl, C$_3$-C$_{15}$alkenyl, C$_7$-C$_{10}$-phenylalkyl, C$_6$-C$_{18}$aryl having 6 to 10 aromatic ring carbon atoms or C$_5$-C$_{12}$cycloalkyl;

R$^3$ is hydrogen, C$_1$-C$_{15}$alkyl or C$_2$-C$_{15}$alkenyl;

n is 1;

A is a residue of a pyridine ring; and

R is one or more of hydrogen, C$_1$-C$_{15}$alkyl, C$_1$-C$_4$-halogenoalkyl, C$_1$-C$_{12}$alkoxy, C$_1$-C$_{12}$alkylthio, phenylthio, benzylthio, C$_1$-C$_{12}$alkylsulphonyl, phenyl, C$_7$-C$_{15}$alkylphenyl, C$_7$-C$_{10}$phenylalkyl, C$_5$-C$_8$cycloalkyl, halogen, NO$_2$, CN, COOH, COO(C$_1$-C$_{12}$alkyl), OH, NH$_2$, CONH$_2$, NHR$^4$, N(R$^4$)$_2$, CONH(R$^4$) or —CON(R$^4$)$_2$ wherein R$^4$ is C$_1$-C$_{12}$alkyl, C$_3$-C$_{12}$alkyl which is interrupted by one or more O-atoms, C$_5$-C$_8$cycloalkyl, benzyl, phenyl or phenyl which is substituted by halogen, C$_1$-C$_4$alkyl, C$_1$-C$_4$alkoxy or NO$_2$, or N(R$^4$)$_2$ is a pyrrolidino, piperidino or morpholine group;

adding said compound to an organic material to be in contact with a metallic surface wherein said organic material is a coating material; and thereby inhibiting corrosion of the metallic surface.

2. A process according to claim 1 wherein the compound of formula I is a compound having the formula IA:

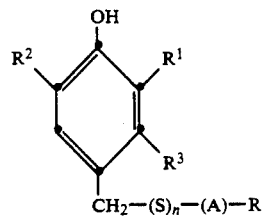

wherein R, R$^1$, R$^2$, R$^3$, n and A are as defined in claim 1.

3. A process according to claim 2 wherein R$^1$ and R$^2$, independently, are hydrogen, C$_1$-C$_{12}$alkyl, C$_7$-C$_{10}$phenylalkyl, phenyl or cyclohexyl.

4. A process according to claim 3 wherein R$^1$ and R$^2$, are C$_1$-C$_5$alkyl and R$^3$ is hydrogen.

5. A process according to claim 1 wherein the organic material is a coating material which contains 0.5 to 5% by weight, based on solids content of said coating material, of at least one compound of formula I.

6. A process according to claim 5 wherein the coating material is a primer for a metallic substrate.

7. A process according to claim 6 wherein the metallic substrate is iron, steel, copper, zinc or aluminum.

8. A process according to claim 5 wherein the coating material is based on an epoxy resin, a polyurethane, an aminoplast, an acrylic-, alkyd- or polyester resin, or a mixture of such resins.

9. A process according to claim 5 wherein the coating material is based on a vinyl polymer, a cellulose ester, a chloro-rubber, a phenol resin, a styrene-butadiene copolymer or a drying oil.

10. A process according to claim 5 wherein the coating material is an aqueous coating material.

11. A process according to claim 10 wherein the aqueous coating material is a cathodically-depositable coating material.

12. A process according to claim 1 wherein the compound of formula I is (3,5-di-tert-butyl-4-hydroxybenzyl)-4-mercaptopyridine.

13. A process according to claim 1 wherein the compound of formula I is (3,5-di-tert-butyl-4-hydroxybenzyl)-2-mercaptopyridine; (3-tert-butyl-5-methyl-2-hydroxybenzyl)-4-mercaptopyridine; (2,3,5-trimethyl-4-hydroxybenzyl)-4-mercaptopyridine; or (3,5-di-tert-butyl-4-hydroxybenzyl)-2-mercaptonicotinic acid.

* * * * *